United States Patent [19]

Quinn et al.

[11] Patent Number: 5,795,469
[45] Date of Patent: Aug. 18, 1998

[54] HIGH PERFORMANCE LIQUID CHROMATOGRAPHY METHOD AND APPARATUS

[75] Inventors: Hubert M. Quinn, Brighton; Rebecca A. Menapace, Framingham; Charles J. Oberhauser, Belmont, all of Mass.

[73] Assignee: Cohesive Technologies, Inc., Acton, Mass.

[21] Appl. No.: 785,324

[22] Filed: Jan. 21, 1997

Related U.S. Application Data

[63] Continuation-in-part of Ser. No. 588,874, Jan. 19, 1996, abandoned.

[60] Provisional application No. 60/027,216 Sep. 30, 1996.

[51] Int. Cl.⁶ ............................................ B01D 15/08
[52] U.S. Cl. ................................ 210/198.2; 210/656
[58] Field of Search .......................... 210/635, 656, 210/659, 198.2

[56] References Cited

U.S. PATENT DOCUMENTS

| | | | |
|---|---|---|---|
| 3,493,497 | 2/1970 | Pretorius et al. | 210/31 |
| 3,869,067 | 3/1975 | Ashmead | 210/198.2 |
| 3,997,298 | 12/1976 | McLafferty | 210/198.2 |
| 4,032,445 | 6/1977 | Munk | 210/198.2 |
| 4,159,284 | 6/1979 | Seko et al. | 585/478 |
| 4,208,284 | 6/1980 | Pretorius | 210/198.2 |
| 4,311,586 | 1/1982 | Baldwin | 210/198.2 |
| 4,389,385 | 6/1983 | Ramsay | 210/198.2 |
| 4,446,105 | 5/1984 | Dinsmore | 210/198.2 |
| 4,454,043 | 6/1984 | Ting | 210/198.2 |
| 4,512,897 | 4/1985 | Crowder | 210/198.2 |
| 4,970,002 | 11/1990 | Ando | 210/659 |
| 5,015,576 | 5/1991 | Nilsson | 210/656 |
| 5,019,270 | 5/1991 | Afeyan | 210/198.2 |
| 5,133,869 | 7/1992 | Taniguchi et al. | 210/656 |
| 5,164,090 | 11/1992 | Hirth | 210/198.2 |
| 5,256,298 | 10/1993 | Powell | 210/660 |
| 5,268,097 | 12/1993 | Girot | 210/198.2 |
| 5,328,603 | 7/1994 | Velander | 210/198.2 |
| 5,401,415 | 3/1995 | Rauh | 210/198.2 |
| 5,503,933 | 4/1996 | Afeyan | 210/198.2 |
| 5,567,307 | 10/1996 | Karmarkar | 210/198.2 |

FOREIGN PATENT DOCUMENTS

| | | | |
|---|---|---|---|
| 359 322 | 3/1990 | European Pat. Off. | 210/198.2 |
| 4018928A1 | 12/1991 | Germany | 210/198.2 |
| WO 95 22555 | 8/1995 | WIPO | 210/198.2 |

OTHER PUBLICATIONS

Patent Abstracts of Japan–vol. 012, No. 079 (P–676) Mar. 12, 1988 & JP 62 218861 (Minoru Koga) 09/26/867–Abstract.

Snyder & Kirkland, *Introduction to Liquid Chromatography*, 2d. Ed. J. Wiley &Sons, Inc., N.Y. (1979), pp. 234–235.

*Primary Examiner*—Ernest G. Therkorn
*Attorney, Agent, or Firm*—Lappin & Kusmer LLP

[57] ABSTRACT

High pressure liquid chromatographic apparatus in which a fluid mixture containing at least one solute that is reactive with chromatographically reactive surfaces in the column is loaded into the column, and a number of plugs of different eluant fluids are injected into that column. The injections are made in a manner that minimizes the amount of eluant required. In one embodiment, the injections are made to insure that flow of at least the eluant fluids through the column will occur, preferably with a substantially flat wave front, at speeds corresponding to reduced velocities greater than about 5,000, i.e. at flow rates sufficient to induce turbulent flow in those fluids, thereby minimizing the time required for the entire succession of mixture and eluant fluids to traverse the column. In other embodiments, the injections are made substantially simultaneously at spatially separated points adjacent the entrance to the column or are made in sequence to a single location adjacent the entrance to the column, in either case the fluids then tend to travel through the column at a common group velocity as closely bunched fluid plugs.

13 Claims, 9 Drawing Sheets

HIGH PERFORMANCE LIQUID CHROMATOGRAPHY METHOD AND APPARATUS

This application is a continuation-in-part of U.S. patent application Ser. No. 08/588,874, filed Jan. 19, 1996, now abandoned, and of U.S. provisional patent application Ser. No. 60/027,216, filed Sep. 30, 1996.

This invention relates generally to chromatography and more particularly to methods and procedures for effecting improved high performance liquid chromatography (HPLC).

BACKGROUND OF THE INVENTION

The separation process effected through high performance liquid chromatography relies on the fact that a number of component solute molecules in a sample stream of a fluid (known as the mobile phase) flowing through a packed bed of particles (known as the stationary phase) usually in a column, can be efficiently separated from one another. Basically, because each individual sample component has a different affinity for the stationary phase, each such component has a different rate of migration through and a different exit time from the column, effecting separation of the components. The separation efficiency is determined by the amount of spreading of the solute band as it traverses the bed or column.

Such separations, particularly in preparative processes, have significant limitations typically occasioned by the batch nature of the processes. Typically, a chromatographic column is first equilibrated by flowing an equilibrating fluid through the column, the latter is then charged or loaded with a fluid mixture containing the solute or solutes sought to be separated, and one or more eluant fluids are flowed sequentially through the column to release bound solute selectively. The eluted solutes are thus temporally separated in the flowstream emerging at the output of the column and the process may be repeated cyclically. At typical flow rates and where the concentration of the desired solutes in the initial fluid mixture are low, the production of significant quantities of the desired solutes can be an unhappily slow and very expensive process with current apparatus and methods that require comparatively long cycle times.

A chromatography system of the prior art, as shown schematically in FIG. 1, typically includes chromatographic column 20 the input of which is usually fed from a plurality of reservoirs provided for storing at least a corresponding plurality of different fluids. Thus, reservoir 22 serves to store a supply of equilibrating fluid 24, while reservoirs 28 and 26 respectively store corresponding supplies of eluant fluid 32 and fluid mixture 30 containing the sample to be separated. Pump 34 is usually coupled between the proximal or input end of column 20 and a plurality of valves means 36, 37 and 38 respectively connected to the outputs of reservoirs 22, 26 and 28, pump 34 serving to force fluid from the various reservoirs into column 20. Disposed adjacent the distal or output end of column 20 is the usual detector 39 of any type well known in the prior art.

In operation, column 20 is usually first equilibrated by opening valve means 36 and running pump 34 so as to permit fluid from reservoir 22 to be pumped at a predetermined flow rate through column 20 to equilibrate the latter. Then, typically valve means 36 is closed and valve means 37 is opened to permit a quantity of fluid mixture 30 to be pumped into column 20, loading the latter with solute molecules that bind to chromatographically reactive surfaces located within column 20. Lastly, valve means 36 and 37 are closed and valve means 38 is opened to permit eluant fluid 32 from reservoir 28 to be pumped through the loaded column. The solute molecules eluted from the column by the eluant fluid are detected, typically optically by detector 39, and may be separated in a known type of fraction collector 35.

The use of several reservoirs for the equilibrating fluids and eluants, all being fed alternatively into the column by a pump through extensive conduit and valve systems, leads to mixing of the various fluids, contributes to band spreading, is wasteful of often expensive eluant fluid, and introduces undesirable delays in operation occasioned by valve switching and the necessity of transferring the volume of unexpended fluids temporarily stored within the conduits and valves. Such delays until very recently have been considered negligible compared to the relatively long cycle time in the column. There is also the inevitable mixing that occurs when the various fluids are introduced into and expelled from the same pump, both the delays and the mixing tending to promote band-broadening and reduce efficiency. The time required ordinarily between the introduction of sample into the column and the ultimate separation of the sample components at the column output can readily exceed many hours and often days.

A major problem impeding speed and throughput of separations in prior art HPLC systems arises out of the use of chromatography columns operating under the constraints imposed by the well-known Van Deemter equations and the consequent arrangement of the physical components of the system.

Because chromatographic system obeying the Van Deemter equations are believed to operate with substantially laminar fluid flow, the fluid wave fronts of the different fluid flows into the column tend to assume paraboloidal configurations, thereby precluding sharp separations between volumes of different fluids traversing the column, contributing to greater mixing. It has recently been discovered that the limitations imposed on such HPLC separations by operation at a mobile phase flow rate dictated as optimal by the Van Deemter curves can be overcome by novel methods of performing liquid chromatography employing an eluant flow rate through the chromatography column at a speed corresponding to an average reduced velocity (as hereinafter defined) greater than about 5000. It is believed that under such conditions, turbulent flow of the eluant is induced within the column and it is postulated that such turbulent flow enhances the rate of mass transfer, thus increasing the throughput/productivity of the column by reducing dramatically the time required to effect separations. These novel methods of and apparatus for performing liquid chromatography are described more fully in U.S. patent application Ser. No. 08/552193 filed Nov. 2, 1995, now abandoned, the same being incorporated in its entirety herein by reference.

It has been customary to describe the function of an HPLC column in a plot in which column plate height H is plotted against linear velocity u of the mobile phase. Since an HPLC process is a diffusion-driven process and since different solute molecules have different diffusion coefficients, one can consider this latter variable in applying the process to a wide range of solutes of different molecular weights. Additionally, the size of the particles in the column may differ from column to column, and may also be considered as another variable. Similarly, the viscosity of the solvent for the solute might be considered. In order to normalize the plots to take these variables into account, one advantageously may employ reduced coordinates. specifically, h in place of H, and v in place of u, as taught by Giddings and described in Snyder & Kirkland *Introduction to Modern Liquid Chromatography*, 2nd Ed., John Wiley & Sons, Inc., (1979) at pp.234–235, to yield a reduced form of the Van Deemter equation as follows:

$$h = a + b/v + cv, \text{ or} \quad \text{(Equ. 1)}$$

$$H = ad_p + bD/u + cud_p/D \quad \text{(Equ. 2)}$$

wherein a, b and c are coefficients, and the coordinate h is defined as $H/d_p$, $d_p$ being the particle diameter; accordingly h is a dimensionless coordinate. Similarly, the dimensionless coordinate, the reduced velocity v, is defined as $ud_p/D$ where D is the diffusion coefficient of the solute in the mobile phase.

It will be recognized that v is also known as the Péclet number. It should be stressed, however, that the reduced coordinate or Péclet number, v, as used in the instant exposition of the present invention, is descriptive of fluid flow through the entire column, and should not be considered as descriptive of fluid flow within the pores of porous particles that may constitute a packed bed in the column.

OBJECTS OF THE INVENTION

A principal object of the present invention is to provide improved chromatographic apparatus and processes for high productivity, high resolution separation of solutes, such as biologicals and the like. Other objects of the present invention are to provide such apparatus and processes as will dramatically enhance the throughput/productivity of preparative chromatography, to provide such apparatus and processes which are sparing of eluant fluids, and to provide such apparatus and processes in which separations are effected in relatively short time within the chromatographic column and in which minimized spatial separation is maintained between bodies of fluids prior to introduction into the column and while those traverse the column.

SUMMARY OF THE INVENTION

To these ends the present invention is directed to novel methods of and apparatus for performing liquid chromatography wherein at least one solute mixture sample is loaded onto a chromatography column and is subsequently eluted from the column by one or more eluant fluids. At least the sample mixture and one or more eluant fluid or fluids are introduced into the column, preferably by rapid injection, at one or more locations adjacent the proximal or input end of the column so that the fluid injections form closely bunched but separated fluid plugs. The fluids may be injected at any reasonable flow rate, but are preferably injected into the column so as to traverse the latter at a high flow rate, preferably at a speed corresponding to an average reduced velocity greater than approximately 5000. The fluids are thus fed directly into the column without any intervening common pump or other device that might tend to promote undesirable mixing prior to introduction of the fluids into the column, and thereafter when in the column in such manner as to maintain minimized spatial step separation between the plugs as the latter traverse said column, even at a speed corresponding to a reduced velocity greater than about 5000.

In one variation of the present invention, desired discrete plugs, as hereinafter defined, of the fluid mixture to be separated and one or more eluant fluids are injected sequentially by separate injectors, the outputs of which are all connected to a common input port located at the input of the column and each of which injectors can be operated to switch injection of fluid plugs rapidly in and out of the main stream of fluid running from the main pump.

Yet another variation of the present invention involves the use of multiple injectors each connected at a separate location spatially separated from one another along the axis of elongation of the chromatographic column and operable to substantially simultaneously inject discrete plugs of the various fluids at the spatially separated locations.

The term "plug" as used herein in connection with injected volumes is to be understood to mean a mass or volume of fluid that is injected into a flowstream in a chromatographic column so as to form a discrete, essentially isomorphic mass extending substantially completely across the column and preferably having approximately flat or planar front and rear surfaces extending perpendicular to the axis of elongation of the column.

The foregoing and other objects of the present invention will in part be obvious and will in part appear hereinafter. The invention accordingly comprises the apparatus possessing the construction and arrangement of parts exemplified in the following detailed disclosure, and the method comprising the several steps and the relation and order of one or more of such steps with respect to the others, the scope of the application of which will be indicated in the claims.

For a fuller understanding of the nature and objects of the present invention, reference should be had to the following detailed description taken in connection with the drawings wherein line numerals denote like parts.

DESCRIPTION OF THE PREFERRED EMBODIMENTS

Figure 1:
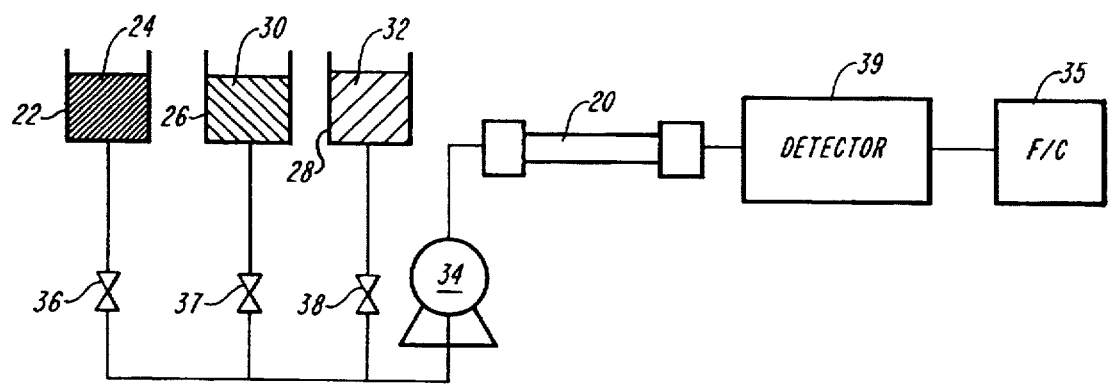
FIG. 1 is a simplified schematic diagram of a typical prior art apparatus.
Figure 2:
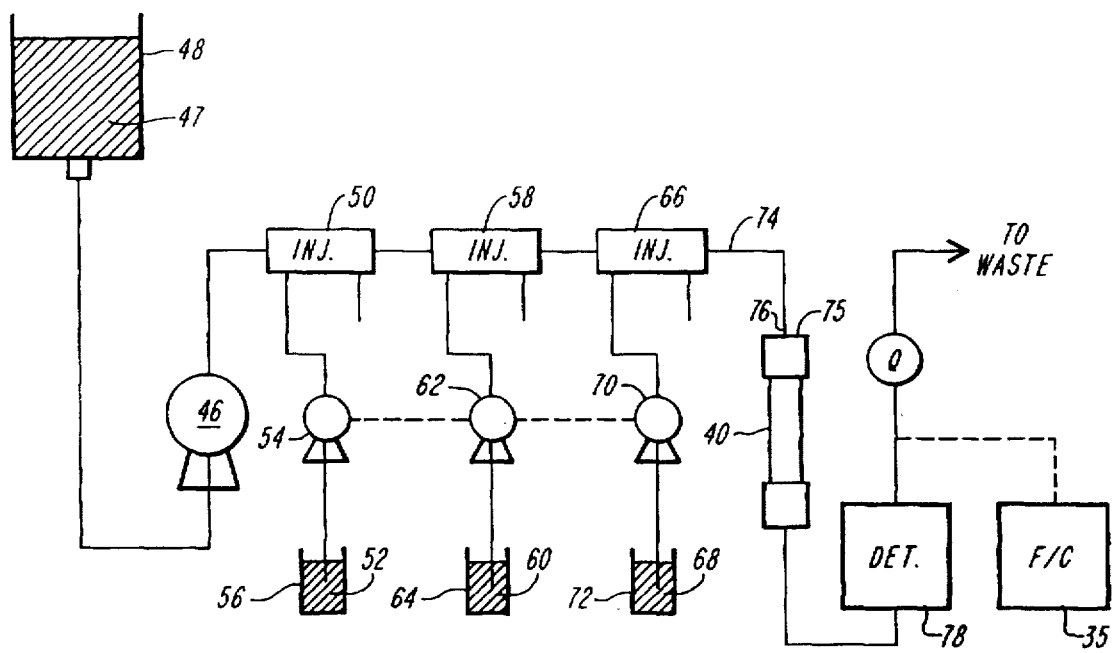
FIG. 2 is a schematic diagram of apparatus embodying the principles of the present invention.
Figure 3:
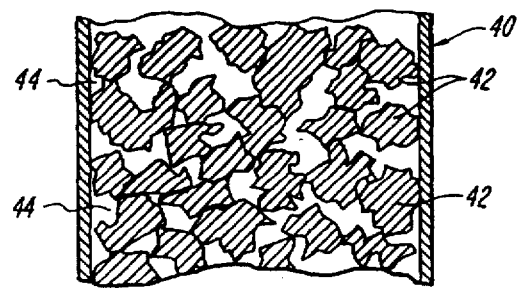
FIG. 3 is an enlarged schematic view in cross-section of a chromatographic column employed in the apparatus of FIG. 2.

One aspect of the present invention, as shown in FIGS. 2 and 3, is embodied in chromatography apparatus comprising a chromatographic column 40 formed as a packed multiplicity of rigid, solid particles 42 having substantially uniform mean diameters of not less than about 30 μm. The term "mean diameter" as used herein is intended to mean the average (mean) diameter or cross-section dimension of the particles regardless of particle configuration and is not to be construed as limited to particles that are necessarily spherical or regular solids, the value of such mean diameter typically being within a distribution of diameters at a confidence coefficient of about 95%. A preferred aspect of the present invention is the irregularity of particles' shape. The term "irregular" as used herein is intended not only to be defined as lacking conformity of form, inasmuch as the particles can be present in a mixed multiplicity of various polyhedral configurations, but is intended to include solids of revolution such as generally spherical, conoidal, ellipsoidal and the like type of particles with rough, uneven or scabrous surfaces.

The particles used in the aforesaid embodiment of the present invention are formed from materials that are incompressible, which term is to be understood to mean that the time rate of changes of the densities and volumes of the particles under pressures of at least about $5\times10^3$ psi, (including outlet column frit retainer) remains substantially zero, and the particles therefore will substantially resist plastic deformation even at such high pressure. The particles of the present invention are shaped and selected in a range of sizes and shapes such that they can be packed at a pressure sufficient to form a column characterized in having interstitial channels 44, as shown particularly in FIG. 3, formed between particles 42. Because of the irregularity of the particles, it will be recognized that the interior walls of such channels are necessarily quite rough in configuration. While it is believed that at least the majority of channels 44 have mean cross-section diameters substantially not less than about 4 μm, the interstitial volume fraction (i.e. the total volume of interstitial channels 44 between the particles) should not be less than about 45% of the total volume of column 40. It will be appreciated that typical columns of the prior art have interstitial volume fractions less than about 45%, more particularly ranging from about 35% to 42%. The surfaces of particles 42 are chromatographically active either per se as is well known in the art, or by treatment, as by coating, with any of the many known chromatographically active, stationary phase layers, also as well known in the art.

Particles 42 may be pellicular, or to increase active surface area, may be porous with the intraparticle pores typically having mean diameters lying within a range of about 60 Å to 5,000 Å. As a result of the particle irregularity, coupled with an interstitial volume fraction of not less than about 45%, it is believed that turbulent flow through the interstitial channels of the column of the present invention can surprisingly be induced at Reynolds numbers well below 10.

In the present invention, means, such as pump 46 coupled to the proximal end of column 40, is provided for pumping a fluid, such as a first equilibrating fluid 47 from an appropriate source such as reservoir 48, flowing through at least a major portion of the interstitial volume in column 40, preferably at a reduced velocity (i.e., $ud_p/D$ as above-defined) substantially above about 5000. The latter is an approximate value at which the slope of the h/v curve begins to decrease along the reduced coordinate h (i.e. $H/d_p$) axis, indicating an improvement in efficiency with increasing reduced velocity. It is believed that turbulent flow of the mixture is induced in the column of the present invention at a flow velocity corresponding to a reduced velocity value of about 5000.

The present invention further includes means, such as loop injector 50 for injecting plugs of fluid sample mixture 52 into column 40. Typically, where the present invention is being employed for preparative purposes, the plug of solute mixture 52 will be as large as practicable to fully load column 40. Mixture 52 contains the solute or solutes of interest, and is pumped into injector 50 by auxiliary pump 54 from another appropriate reservoir or storage tank 56.

Figure 10:
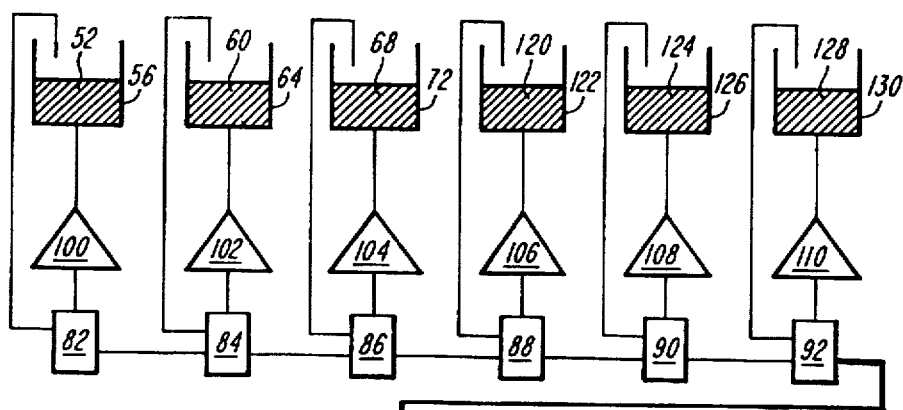
FIG. 10 is a schematic representation of an embodiment of an apparatus embodying the principles of the present invention.
Figure 11:
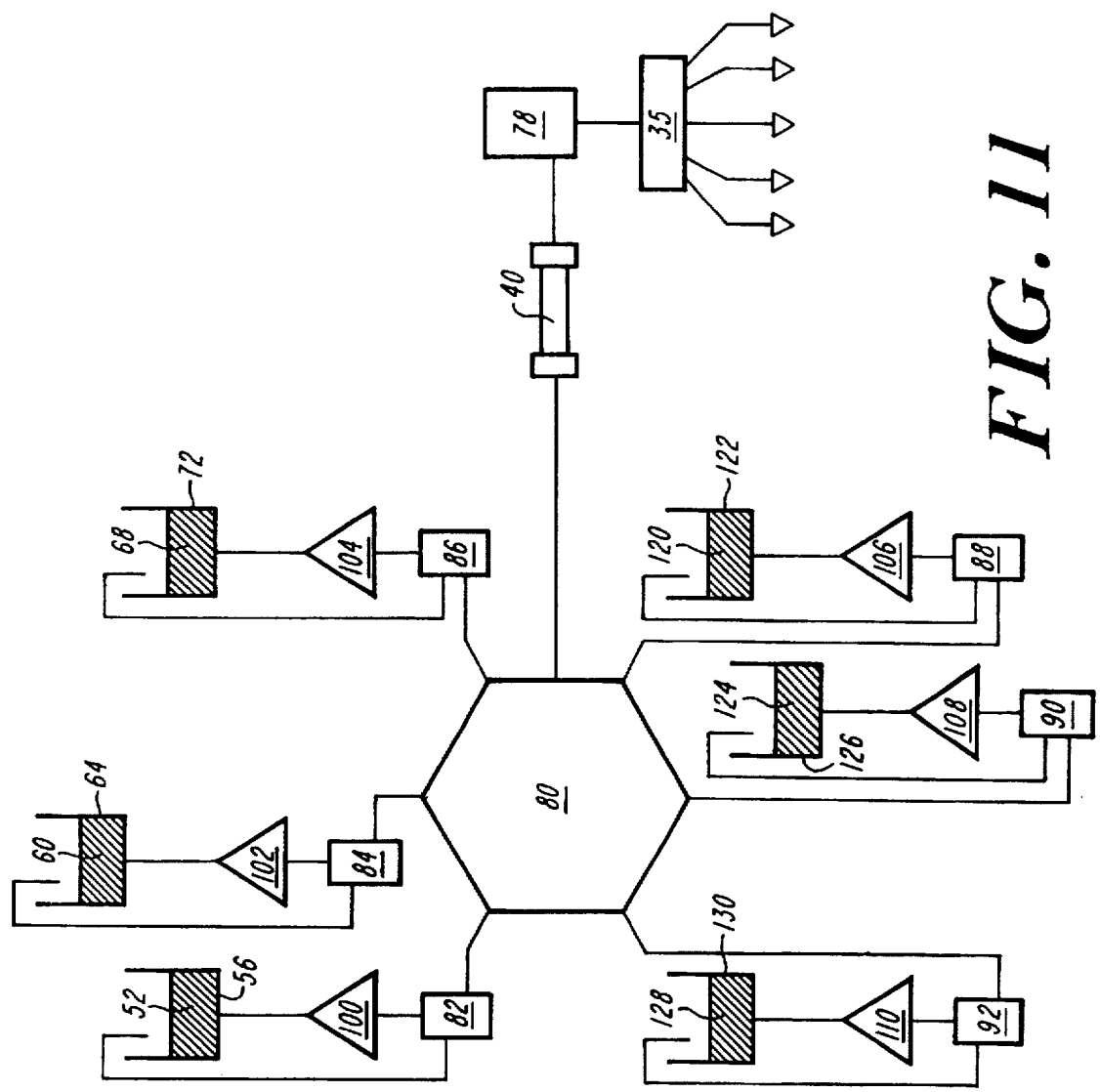
FIG. 11 is a schematic representation of an embodiment of an apparatus embodying the principles of the present invention.
Figure 12:
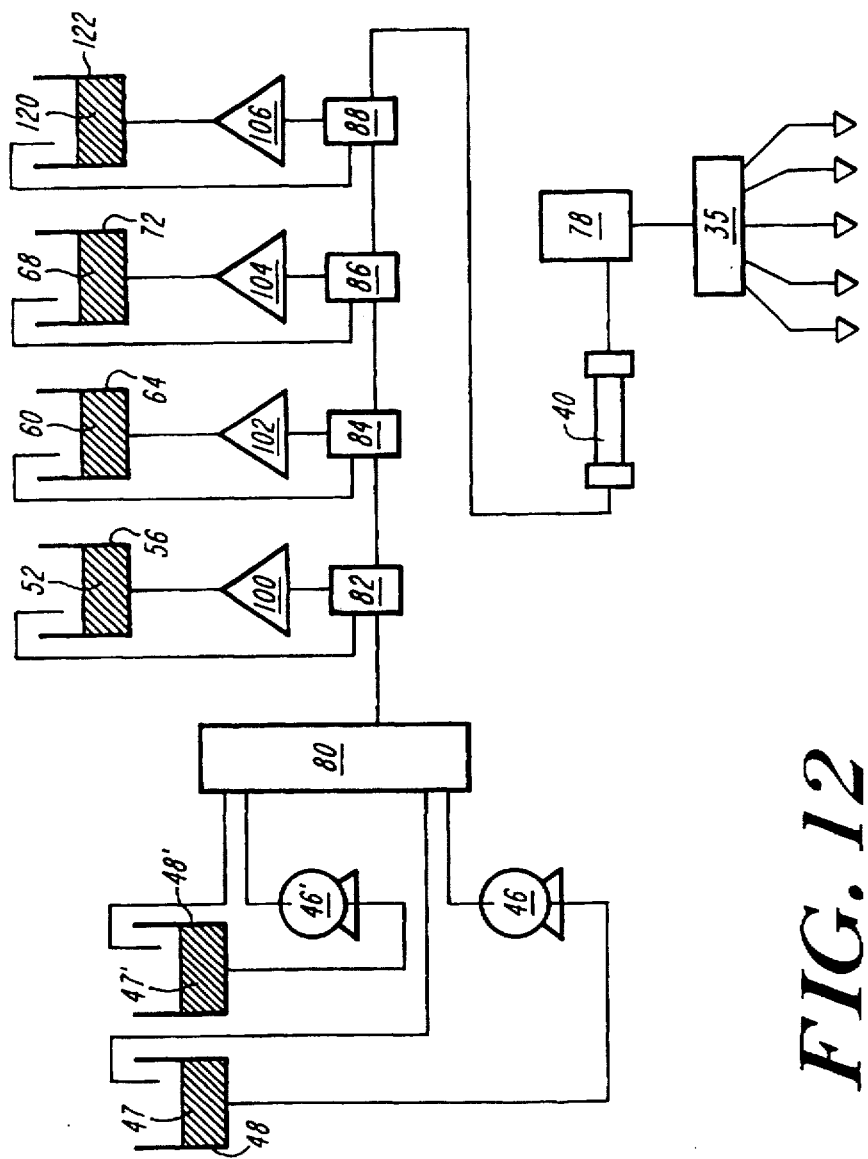
FIG. 12 is a schematic representation of an embodiment of an apparatus embodying the principles of the present invention.

The present invention also includes means, such as at least one loop injector 58 for flowing eluant fluid 60 into column 40. Fluid 60 is pumped into injector 58 by another auxiliary pump 62 from another appropriate reservoir or storage tank 64. In the embodiment shown in FIG. 2, yet another loop injector 66 is also shown for injecting a second eluant fluid 68 into column 40. The latter is fed into injector 66 by a third auxiliary pump 70 from another appropriate reservoir or storage tank 72. It will be appreciated that pumps 46, 54, 62 and 70 may be any desired type of known pump and are not to be limited to mechanical pumps, but may be any known system for imposing pressure on the respective fluid to cause the latter to flow at the desired flow rate. It will be understood that additional injectors for other eluant fluids may also be provided as desired. For example, FIGS. 10 through 12 depict embodiments that include additional eluant fluids 120, 124, and 128, in reservoirs 122, 126, and 130, respectively, in a variety of configurations to allow optimal flexibility in delivery of a particular eluant fluid to the flow path of the chromatographic system of the invention.

Any injection means may be employed to apply sample and eluant fluids to column 40 in accordance with the present invention, so long as the means allows a measured amount of fluid to be delivered into the flow path. For example, the injection means may include a loop injector or a section of tubing, in combination with a pump means. Alternatively, the injection means may be driven by the action of gravity applied to the flow path.

In the embodiment shown in FIG. 2, input conduit 74 is coupled from the output of pump 46 to input end 75 of column 40, and injectors 50, 58, 66 are all connected to input conduit 74 at different locations spaced apart from one another between pump 46 and input end 75 of column 40. Operation of each injector can be manually controlled or automatically controlled to inject respective plugs of sample mixture 52 and eluant fluids 60 and 68 into the proximal end of column 40, preferably at speeds corresponding to reduced velocities above about 5000. In accordance with the invention, manually controlled operation of the injectors encompasses operation mediated by human intervention, either to perform loading of the injector, to perform injection of the sample or eluant fluid into the flow stream of the system into the column, or to perform both aspects of the injection process. Automatically controlled operation of injectors is defined herein as operation which does not require human intervention to perform loading of injectors and/or injection of sample or eluant fluid into the flow stream of the system into the column. In the preferred embodiment, the automatically controlled injectors are operated by actuators such as motors which are operated under the control of a computer system. An automatically controlled injector of the invention may also include a manually operated injector as a backup to the automatically controlled injector. The apparatus of the invention may optionally include both manually controlled and automatically controlled injectors.

The injectors may be operated to inject the respective fluid plugs substantially simultaneously or in a timed sequence. For example, where the injection coil, as hereinafter described, in injector 50 is sized to deliver a 100 mL plug, the corresponding coils in injectors 58 and 66 may be sized to provide plugs of, for example, 5 mL each of eluant fluids, and generally would have injection coils with correspondingly smaller volumes. In such case, it is desirable to place sample injector 50 at a location more remote from the input end of column 40 than the other injectors to avoid having to inject the small amounts of eluant into column 40 through the large diameter coil conduit in injector 50 and avoid the consequent mixing that would tend to occur. FIG. 10 depicts a configuration of the chromatography apparatus of the invention in which the sample injection means 100 and eluant injection means 102, 104, 106, 108, and 110 are connected in series, and the sequence of operation of the various injection means is controlled by flow switching valve means 82, 84, 86, 88, 90, and 92. In FIG. 11, sample injection means 100 and eluant injection means 102, 104, 106, 108, and 110 are connected in such a way that sequential delivery of the various fluids to the flow path is accomplished, under the control of flow switching valve means 82, 84, 86, 88, 90, and 92. The embodiment of FIG. 12 depicts a configuration that allows delivery of a second equilibrating fluid 47' to the flow path from reservoir 48', through the action of pump means 46'. Valve means 80 operates upstream of flow switching valve means 82, 84, 86, and 88, for example, to apply an elution gradient to the flow path. It will be apparent that the spacing and location of the sample and eluant injectors relative to the column and any input conduit thereto may be other than that shown in the drawings.

Injection in preparative LC is particularly important inasmuch as loading of the sample across the entire column cross-section is generally preferred as permitting better use of the total column packing. In the present invention, sample inlet distributing head 76 is positioned at the input end of column 40 and employed to distribute the injected volumes as plugs with preferably a substantially flat or planar surface or front perpendicular to the axis of elongation of the column, not only for the foregoing reasons but and also to maintain a relatively sharp surface of demarcation between adjacent plugs of fluid. Fluid is introduced into head 76 at a pressure that will ensure that the plug or volume injected into column 40 is moving at substantially the same velocity as the flowstream generally, thereby minimizing mixing of adjacent plugs of fluids and preserving the approximate planarity of the ends of each plug where the plugs are adjacent to one another.

The plug of mixture 52 flowing through column 40 serves to load the latter as solute molecules become bound to chromatographically active surfaces in the column. The solute molecules eluted from the column by the eluant fluid are detected, typically optically by detector 78, of a type and in a manner well known in the prior art, disposed at the distal end of column 40. For superior results, the eluant flow through column 40 is preferably at a velocity corresponding to a reduced velocity of above about 5000, so that band spreading of solute eluted by the eluant fluid from the column in the present invention is an inverse function of the Reynolds number for the eluant fluid and a direct function of the magnitude of the diffusion coefficient of the solute in the eluant fluid. It should be understood, however, that the present invention is applicable to chromatography in which the flowstreams through the column are laminar inasmuch as the present invention tends to minimize the amount of eluant employed in either case.

In one embodiment of the present invention, column 40 is formed by packing particles having a mean diameter not less than about 30 µm, preferably under pressure of at least about $5\times10^3$ psi to insure that the column formed will include substantially no voids except for interstitial channels 44 formed between particles 42 in contact with one another, i.e. column 40 has a substantially uniform bulk density. Columns 40 formed in this manner, regardless of whether or not the particles are porous or non-porous, should exhibit interstitial fractions of about 45% or higher. Lower interstitial fractions, typically around 35% for porous, non-rigid polystyrene particles, will not exhibit the requisite reduced fluid velocity except at unacceptably high pressure that will tend to collapse or rupture the particles.

In order to insure the formation of the desired uniform density column with the preferred interstitial fraction and preclude collapse under operating pressure, the particles used to pack a column in the present invention are rigid solids that must necessarily be incompressible at packing pressure of at least about $5\times10^3$ psi, preferably up to pressures as high as about $1\times10^4$ psi. To that end, the preferred particles are formed from materials such as alumina, titania, silica, zirconia, vanadia, carbon and combinations thereof.

The method of the present invention therefore requires that the flow through at least a majority of the interstitial channels in the chromatographic column must be turbulent. It is postulated that the turbulent flow profile is almost flat, as distinguished from the typical parabolic flow profile characteristic of laminar flow through a chromatographic column. More importantly, it is believed that when turbulent flow is induced, a radial component of velocity is superimposed upon the normal diffusion process, altering the normal diffusional process and the band-spreading kinetics in a favorable manner with respect to the efficiency of the column. It is further postulated that in order to induce and sustain turbulent flow through the column, there is a critical relationship between the diameter of the flowing channel and the linear flow velocity. The need for particles that are rigid and can withstand changes in pressure without plastic deformation, as above-indicated, is therefore very important in such case.

Injectors useful in the present invention are commercially sold as, for example, Model 3725 and Model 3725-038 manual injectors available from Rheodyne Incorporated of Cotati, Calif., Model E-45 automatic injectors available from Valco Instrument Company, Inc. of Houston, Tex., and similar injectors provided by these and several other manufacturers. A schematic diagram of a typical double-loop injector of such type, employing the symbols used by the manufacturer, is shown in two alternative states in FIGS. 4 and 5. In each such Figure, the injector includes first input port 80 connected to the output of main pump 46, first injector loop coil 82, first output port 84 connected to input end 75 of column 40, second input port 86 connected to the output of auxiliary pump 54, second injector loop coil 88, and second output port 90 which discharges to waste, and means for switching or valving the various input and output ports through different loop coils.

Figure 4:
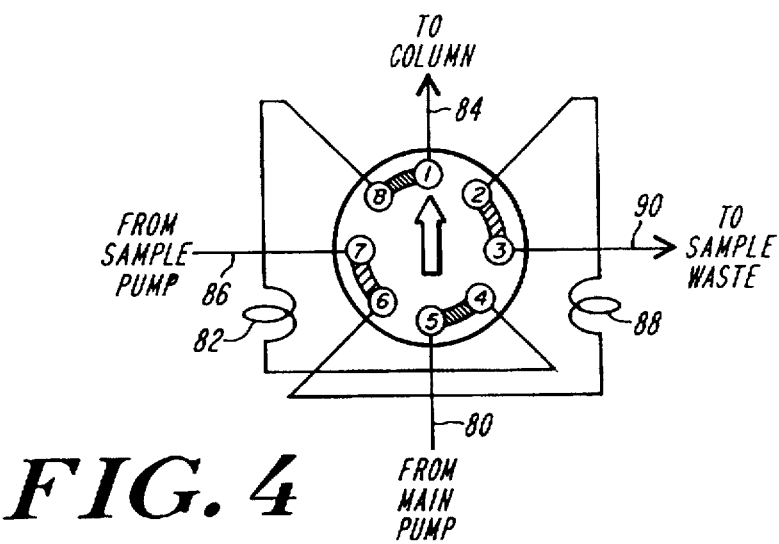
FIG. 4 is a schematic representation of a typical dual-coil injector useful in the present invention and shown in a first state.

The operation of the injector of FIGS. 4 and 5 can be advantageously described in connection with injection of sample fluid from reservoir 56 but it is to be understood that the description applies equally as well to injection of eluant fluid from corresponding reservoirs. Thus, in operation, it can be initially assumed that in the first state of the injector as shown in FIG. 4, coil 82 is already filled with sample fluid 52. In FIG. 4, the internal valving of the injector is shown as connecting input port 80 to one side of coil 82, the other side of the latter being connected to output port 84. Thus, as fluid pumped by pump 46 is introduced abruptly, by the switching or valving action of the injector, into and through port 80, the fluid pressure imposed serves to hydraulically force the sample fluid out of coil 82, replacing the sample fluid with fluid 47 from reservoir 48, and injecting the sample fluid from coil 82 through port 84 into column 40 as a plug. This switching action of the injector also serves to connect input port 86 to one side of second loop coil 88, filling the latter as loop coil 82 is emptied of sample fluid, the other side of coil 82 being connected to port 90 so that any excess sample fluid is discharged to waste through port 90.

Figure 5:
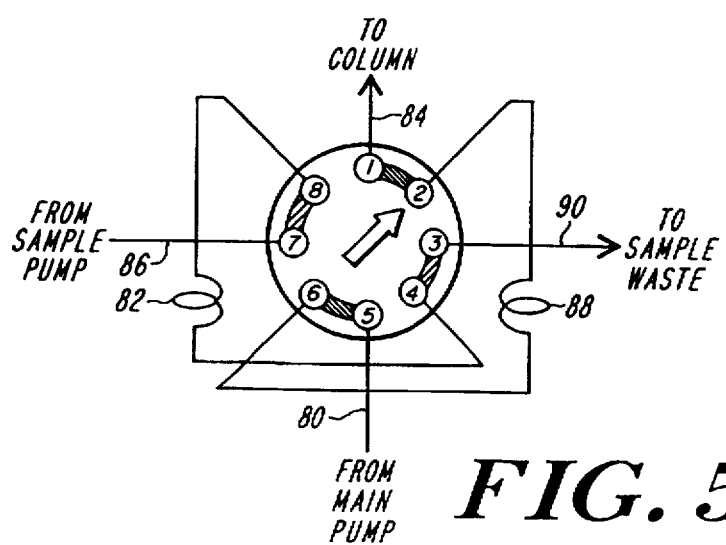
FIG. 5 is a schematic representation of the dual-coil injector of FIG. 4, in a second state.

As shown in FIG. 5, when the injector is switched to its second state, the internal valving of the injector is shown as connecting input port 80 to one side of coil 88, the other side of the latter now becoming connected to output port 84. Thus, as fluid pumped by pump 46 is again introduced abruptly, by the switching or valving action of the injector, through port 80, the fluid pressure imposed serves to force hydraulically the sample fluid contained in coil 88 out through port 84 into column 40 as another plug. This switching action of the injector also serves to connect input port 86 to one side of first loop coil 82 filling the latter with sample fluid again. The other side of coil 82 becomes connected to output port 90 so that any excess fluid is discharged to waste. The injection of plugs of fluid 52 into column 40 are typically followed with injections of one or more plugs of eluant fluids 60 and 68, or by a flow of fluid 47 that will occur simply by permitting a flow of the latter to proceed seriatim through one or more of the several injectors.

Figure 6:
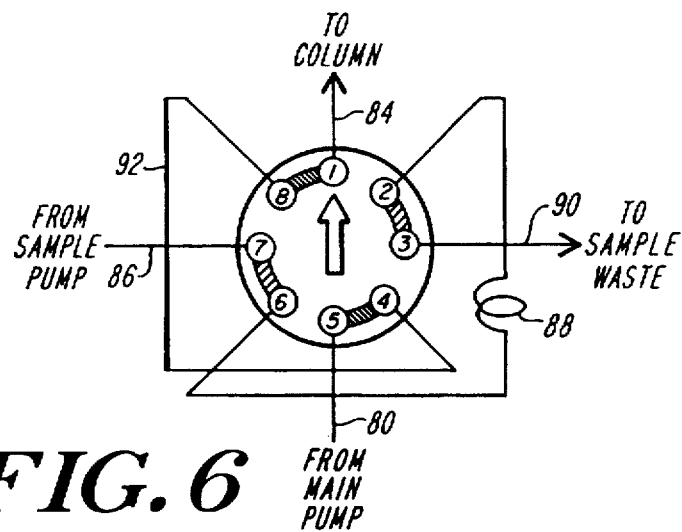
FIG. 6 is a schematic representation of a single coil injector useful in the present invention and shown in a first state.
Figure 7:
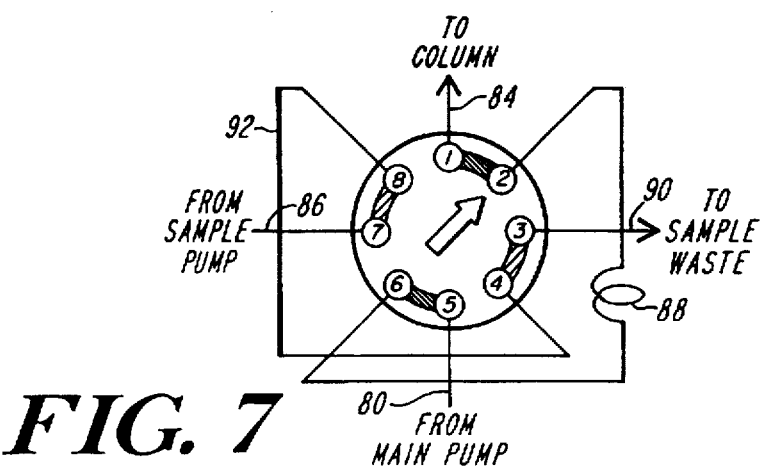
FIG. 7 is a schematic representation of the injector of FIG. 6, in a second state.

While the structure and operation of the injectors has been described in terms of double loop coil injectors, it will be understood that it is not so limited. For example, as shown in FIGS. 6 and 7 wherein like numbers denote like parts, single loop injectors with by-pass switching can also be employed. In FIGS. 6 and 7, all of the parts of the injectors are identical to those of FIGS. 4 and 5 except that a by-pass conduit 92 of minimal storage capacity is used to replace loop coil 82. It will be apparent that yet other known types of injectors can also be advantageously employed in the apparatus of the present invention.

Switching operation of a plurality of injectors is preferably under the control of means, such as a known computer or controller to optimize switching time and obtain the desired sequence of plug injections into column 40. Injectors of the type described are preferred inasmuch as they tend to provide desirably sharp transition boundaries between adjacent plugs of fluid, thus reducing mixing.

Figure 8:
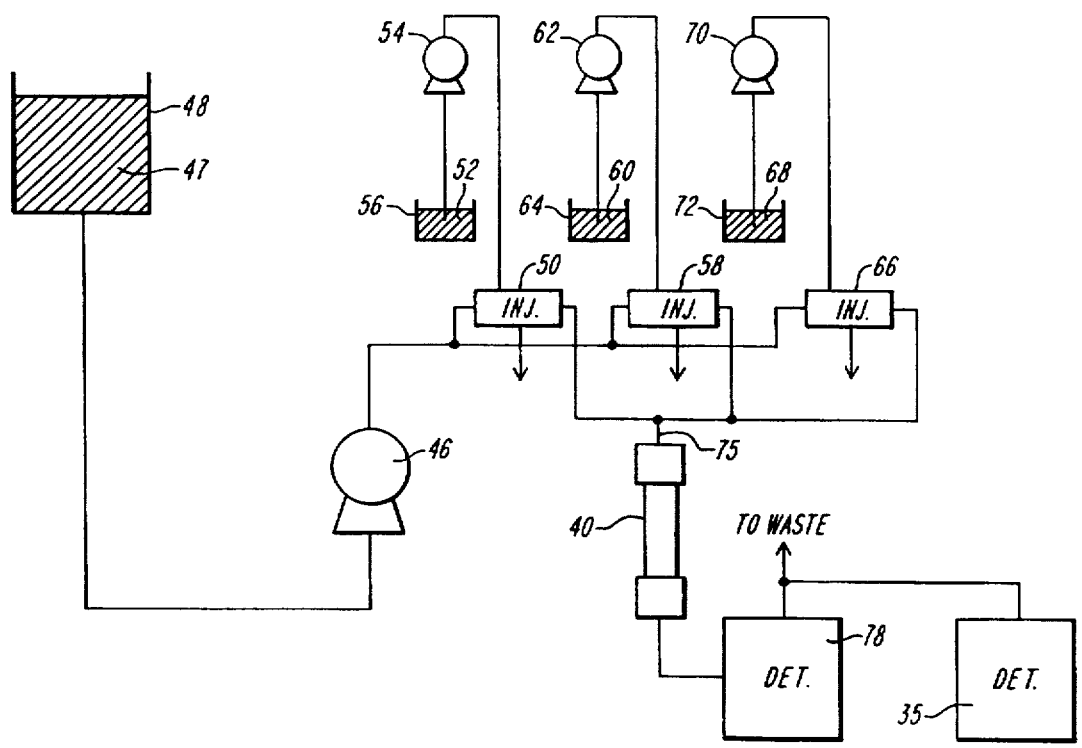
FIG. 8 is a schematic representation similar to the embodiment of FIG. 2, but wherein all injectors feed a single input to the chromatographic column.

As shown in FIG. 2, injectors 50, 58 and 66 are coupled to input conduit 74 to column 40 at spaced-apart locations, and it will be understood that in such case, all of those injectors can be operated simultaneously by means such as an appropriately programmed computer, to provide a succession of spatially separated plugs presented to head 76 or may be operated serially to provide even more flexibility in spacing the location of the plugs as the latter transit column 40. Yet, as shown in FIG. 8, wherein like numerals denote like parts, all of the injectors may be coupled directly to port 75 or a single location on conduit 74, and in such case, all of those injectors can be operated serially to provide a succession of spatially separated plugs presented to head 76.

Figure 9:
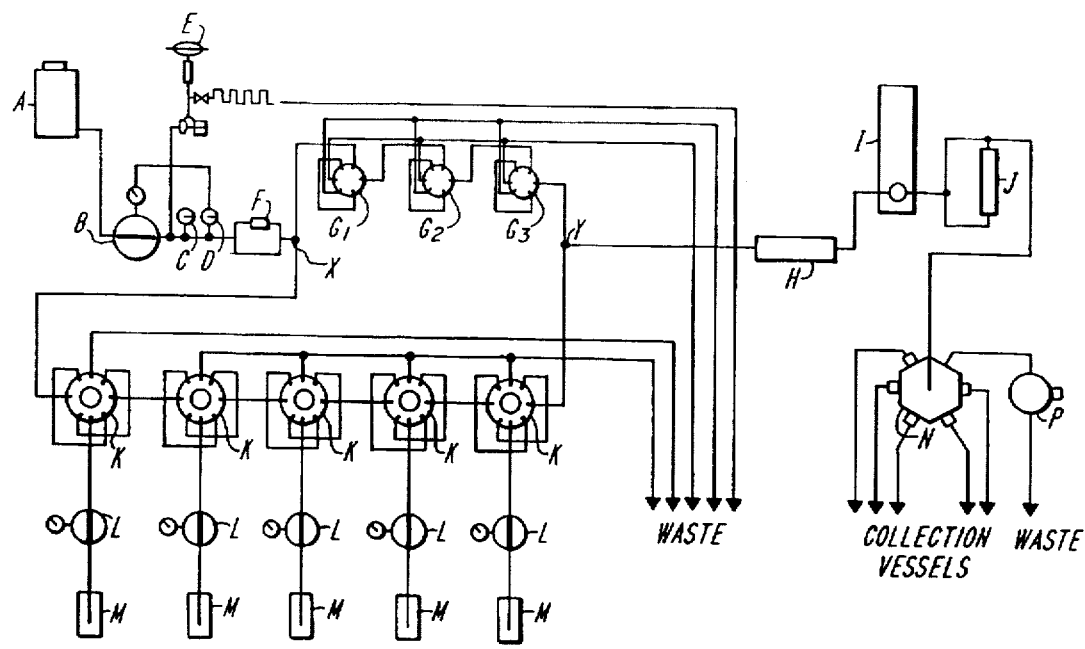
FIG. 9 is a schematic representation of an embodiment of an apparatus embodying the principles of the present invention.

In the embodiment depicted in FIG. 9, solvent reservoir A is in fluid communication with main pump B, which withdraws equilibrating fluid from reservoir A and delivers said fluid, under pressure, to column H. A quick disconnect junction may optionally be included upstream of main pump B in order to allow the end of tubing connecting reservoir A and main pump B to be sealed to avoid or to minimize leakage and spillage should either occur. Main pump B may be any suitable pump means, preferably embodied as a single-headed pump coupled to a pressure gauge C, pressure sensor or transducer D, and pulse dampener E. Pressure at the outlet of main pump B is monitored using pressure gauge C and pressure transducer D in combination with an internal pressure switch which shuts down the system if the pressure is above a predetermined value. Main pump B should be capable of delivering the mobile phase of the chromatography system at a ripple-free, user-selected flow rate. When a single headed pump is used, a pulse dampener E is included to minimize ripples or pulsations in flow rate which may occur. Pulse dampener E preferably includes a pressurized tetrafluoroethylene (TFE) membrane which flexes during the delivery cycle of main pump B and which is restored during the "refresh" cycle of pump operation. The pressure applied to the membrane of pulse dampener E is dependent on the pressure at which main pump B is operated, being equal to about 80% of the operating pressure of main pump B.

An inline filter F is placed downstream of pressure transducer D to remove particulate matter from the mobile phase. Preferably a filter capable of removing particles greater than about 0.5 µm in diameter is employed, though other filters may also be used in accordance with the invention.

Downstream of inline filter F is an inlet valve X and an outlet valve Y which selectively establish a first flow path and a second flow path, outlet valve Y being in fluid communication with column H. In accordance with the invention, the first flow path is in parallel to the second flow path, and each flow path includes at least one injector valve.

Preferably, a plurality of manual injector valves is provided along the first flow path, as is exemplified in FIG. 9 by valves $G_1$, $G_2$, and $G_3$. The manual injector valves are preferably provided in series with each other, wherein the outlet of each downstream valve is in fluid communication with the inlet of the adjacent upstream valve (e.g., the outlet of valve $G_1$ is in fluid communication with the inlet of valve $G_2$ and the outlet of valve $G_2$ is in fluid communication with the inlet of valve $G_3$). Sample or eluant may be added to the system through any of manual injector valves $G_1$, $G_2$, and $G_3$, in accordance with the present embodiment. The manual injector valves of the first flow path may be used to determine the flow parameters of a specific chromatographic purification empirically, prior to use of the automatic injection valves K for the purification. The volumes accomodated by manual injector valves $G_1$, $G_2$, and $G_3$ may be the same or they may differ in accordance with this embodiment. Each of manual injector valves $G_1$, $G_2$, and $G_3$ is filled via a needle port in the valve handle assembly, which depicts separate LOAD and INJECT positions. Fluid is injected into the manual injector valve while the valve handle is in the LOAD position, using a syringe or other suitable cannula having a square end. The valve handle is rotated to the INJECT position to inject the fluid from the valve into the flow path to column H.

Preferably, a plurality of automated injector valves K is provided in series along the second flow path between X and Y, as is depicted in FIG. 9. Sample or eluant fluid is injected from reservoirs M into the second flow path using a pump L in fluid communication with each automated injector valve K, as exemplified in FIG. 9. Each pump L is under the control of a suitable means. such as a computer program. which determines the time of each injection and the flow rate of fluid pumped. A flowmeter may optionally be included between each pump L and the respective injector valve K to monitor fluid flow into each automated injector valve.

The column H employed in this embodiment is as described above in relation to the column depicted in FIG. 3. A detector I is included downstream of column H to detect species that elute from column H. A flowmeter J may optionally be included downstream of detector I, to monitor flow of the mobile phase through the system. Similarly, valves N (which are preferably solenoid valves) are included downstream of detector I to divert the eluant stream to a collection vessel. A valve P is also included downstream of detector I to divert the eluant flow into a waste vessel.

While the apparatus of the present invention has been described in terms of a chromatographic column of packed particles, as described in the aforementioned U.S. patent application Ser. No. 08/552193, the columns useful in the present invention can also be in the alternative form of a capillary tube defining a hollow, elongated channel of substantially uniform internal diameter, the channel being provided with a chromatographically active interior surface. The tube is formed such that turbulent flow will be induced in fluid pumped through the interior at a velocity sufficient to create centrifugal forces in the fluid.

It has been found with apparatus of the present invention that a complete cycle involving 100 mL sample plugs, using two different 5 mL eluant can be run within about 15 seconds, providing an extremely high throughput. With the apparatus and method of the present invention, the amount of eluting solvent required for a given volume of sample, is generally considerably less. For example, for a 1×10 cm column with a nominal volume of 8 mL, the amount of eluant used in the prior art is typically about 40 mL. For the present invention using a like column, this eluant volume is reduced to not more than about 8 mL, a substantial reduction by a factor of about 5 of often expensive eluant.

Figure 13:
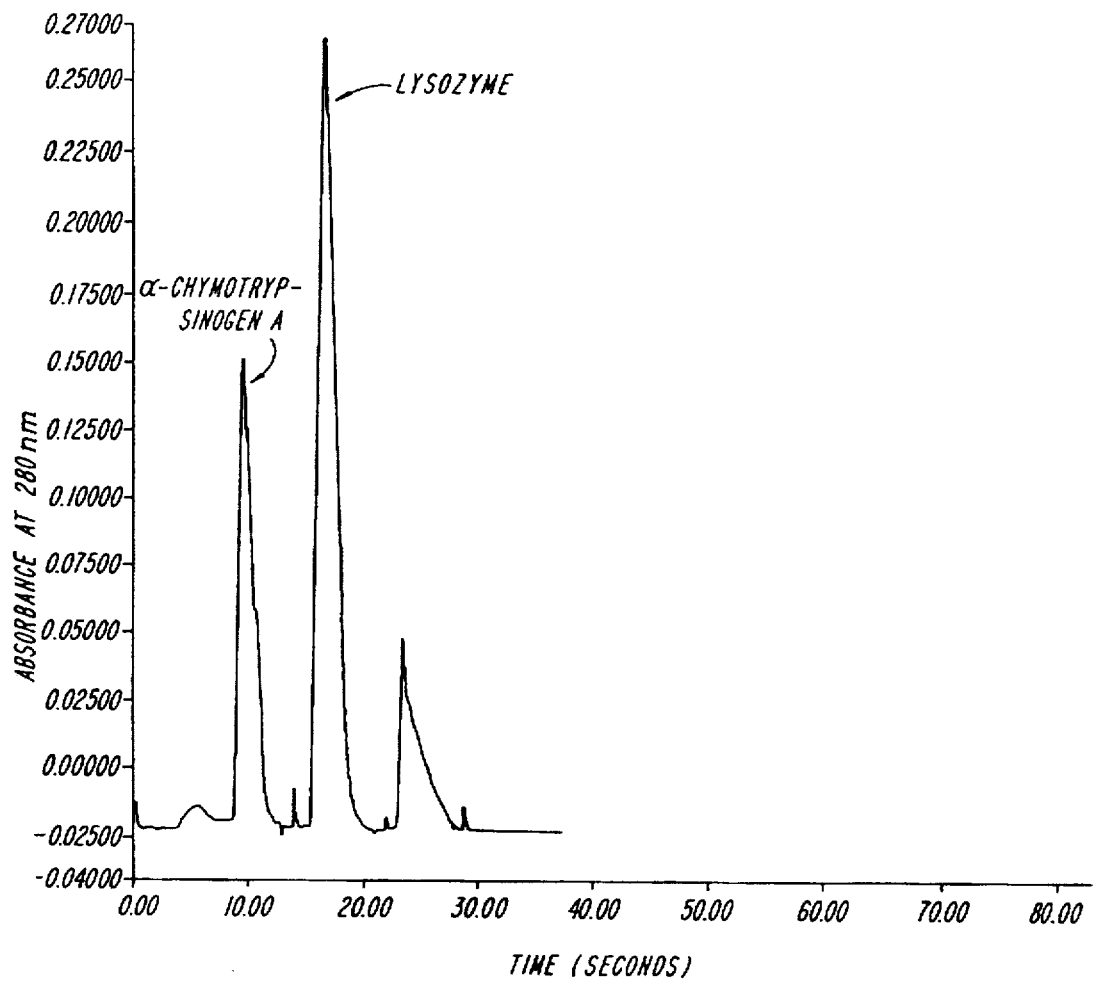
FIG. 13 is a chromatogram illustrating a preparative separation using the apparatus of the invention.

FIG. 13 demonstrates a preparative separation of α-chymotrypsinogen A from lysozyme, using the apparatus of the invention. For this separation, a cation exchange column equilibrated with phosphate buffer (pH 8) was employed. The proteins were sequentially eluted using varying amounts of NaCl dissolved in phosphate buffer (pH 8), α-chymotrypsinogen eluting with 200 mM NaCl and lysozyme eluting with 2M NaCl. After separation of the two proteins, a cleaning step was performed using NaOH, allowing cyclic repetitions of the separation to be performed in accordance with the present invention.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. In chromatography apparatus including a substantially uniform, elongated chromatography column containing chromatographically reactive surfaces, means for injecting into said column a discrete volume of liquid mixture containing at least one solute that is reactive with said surfaces so as to load said column, and means for flowing eluant fluid through the loaded column, the improvement wherein:

said means for flowing said eluant fluid comprises means for injecting at least one discrete plug of said eluant fluid into said column adjacent the input of said column so as to maintain minimized spatial step separation between said plug and said discrete volume of liquid mixture as said plug and volume traverse said column wherein said column and said means for flowing are configured such that the flow of said volume of eluent traverses said column at a reduced velocity greater than 5000.

2. Chromatography apparatus as defined in claim 1 wherein said means for injecting provides said plug traversing said column with a substantially plane front extending substantially perpendicularly to the axis of elongation of said column.

3. Chromatography apparatus as defined in claim 1 wherein said means for injecting provides said plug traversing said column with a substantially plane end extending substantially perpendicularly to the axis of elongation of said column.

4. Chromatography apparatus as defined in claim 1 wherein said means for injecting comprises a plurality of individual injectors for injecting respective plugs of said eluant fluid and said liquid mixture.

5. Chromatography apparatus as defined in claim 4 wherein said injectors are positioned for injecting a plurality of different plugs at respective spatially separated positions along an extension of the axis of elongation of said column so that said plugs traverse said column as closely bunched fluid plugs.

6. Chromatography apparatus as defined in claim 5 including means for controlling said injectors so that the latter operate for injecting said respective plugs substantially simultaneously.

7. Chromatography apparatus as defined in claim 4 including means for controlling said injectors so that the latter operate for injecting said respective plugs sequentially.

8. Chromatography apparatus as defined in claim 7 wherein said injectors are positioned for injecting plurality of different plugs as sequential injections effected at one position located adjacent the input of said column.

9. Chromatography apparatus as defined in claim 7 wherein said injectors are positioned for injecting a plurality of different plugs at respective spatially separated positions along an extension of the axis of elongation of said column so that said plugs traverse said column as closely bunched fluid plugs.

10. Chromatography apparatus as defined in claim 4 including means for cyclically repeating the injections of said plugs of eluant fluid and mixture.

11. Chromatography apparatus as defined in claim 10 including means for effecting a flow of a predetermined volume of equilibrating fluid through said column between cyclic repetitions of said injections.

12. Chromatography apparatus as defined in claim 10 wherein said means for injecting comprises at least first and second injectors connected for injecting respective said plugs at respective first and second spatially separated positions along an extension of the axis of elongation of said column, and at least third and fourth injectors connected for injecting respective said plugs at third and fourth spatially separated positions, said apparatus including means for controlling the injections by said injectors for cyclically alternating injections of said respective plugs by said first and second injectors at said first and second positions, with injections of said respective plugs by said third and fourth injectors at said third and fourth positions.

13. Chromatography apparatus as defined in claim 12 wherein said third and fourth positions are the same as said first and second positions.

* * * * *